United States Patent [19]

Teague

[11] 4,342,451
[45] Aug. 3, 1982

[54] COMBINATION CAST CHAIR AND SPICA TABLE

[76] Inventor: Ross L. Teague, 11313 Bel Air Pl., Oklahoma City, Okla. 73120

[21] Appl. No.: 188,434

[22] Filed: Sep. 19, 1980

[51] Int. Cl.$^3$ .............................................. A61F 5/04
[52] U.S. Cl. ................................... 269/328; 269/322; 128/84 B
[58] Field of Search ............................... 269/322–328, 269/88; 297/92, 93, 345, 353, 443; 128/84 R, 84 B

[56] References Cited

U.S. PATENT DOCUMENTS

| | | |
|---|---|---|
| 2,057,992 | 10/1936 | Wiruth. |
| 2,204,266 | 6/1940 | Wilcox. |
| 2,614,558 | 10/1952 | Lovell. |
| 2,658,507 | 11/1953 | Neufeld ............................. 128/84 B |
| 3,509,876 | 5/1970 | Pilz ..................................... 269/328 |
| 3,528,413 | 9/1970 | Aydt. |
| 3,745,996 | 7/1973 | Rush ................................... 128/84 B |

*Primary Examiner*—Robert C. Watson

*Attorney, Agent, or Firm*—Robert K. Rhea

[57] ABSTRACT

A generally upright open framework, having patient forearm and hand supports and having a horizontal seat intermediate its height, is supported by a platform mounted on a vertically adjustable pedestal base. Back and torso support members, telescopically received by sockets on the platform, form a back rest when the frame is in cast chair position. Base supported universal joint connected foot rests support the feet and legs of a seated patient. The back and torso members are movable to a second position on the platform to form a torso and head support for a supine patient. Telescopic tube extensions are supported by other sockets on the platform and include universal joint connected feet enveloping members for supporting the feet and legs of a supine patient when the frame is in spica table position. Substantially all components forming the frame and supports for a patient or his limbs are movable toward and away from the platform and relative to each other when supporting a patient, either seated or supine, for casting, splinting or bandaging the torso and/or limbs.

9 Claims, 7 Drawing Figures

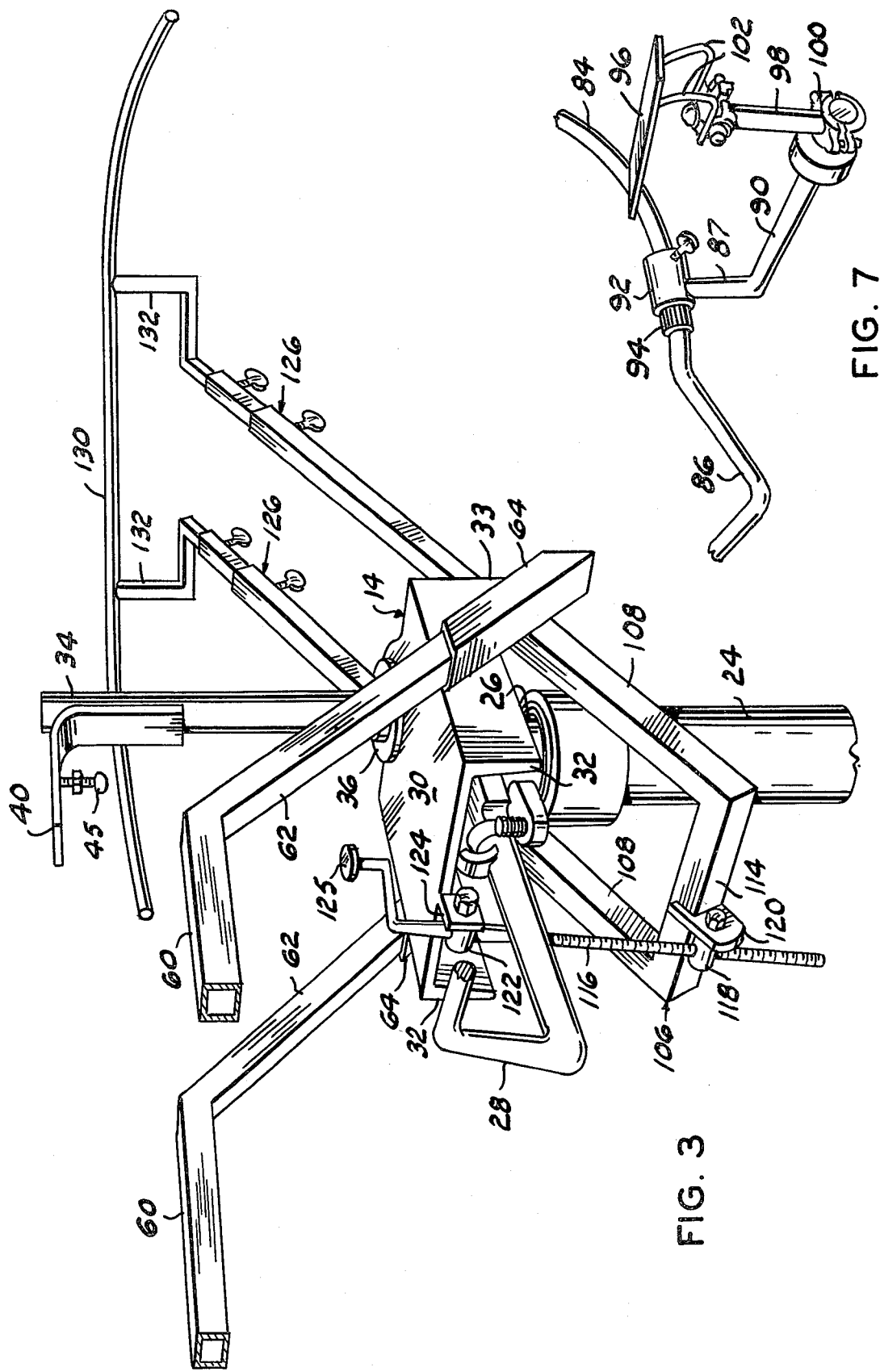

COMBINATION CAST CHAIR AND SPICA TABLE

BACKGROUND OF THE INVENTION

1. Field of the Invention

The present invention relates to medical appliances and more particularly to a combination cast chair and spica table for a patient suffering from skeletal fracture.

2. Description of the Prior Art

Prior patents generally disclose appliances for supporting one injured limb of a patient, such as an arm or leg.

U.S. Pat. Nos. 2,614,558 and 3,528,413 disclose arm supporting devices which may be clamped to an operating table, or the like, for casting the forearm or portions thereof.

U.S. Pat. Nos. 2,057,992 and 2,204,266 are examples of bed attached and free standing leg supporting devices for casting broken bones and/or providing traction.

This invention is distinctive over prior art devices by combining the desirable features of supporting a patient in a seated or supine position in which the device is adjustable for supporting any or all fractured limbs of the patient in any required position for applying splints, bandages or casts and in which the device is vertically adjustable with respect to a supporting surface.

SUMMARY OF THE INVENTION

A floor supported pedestal forms a base having a central upstanding shaft vertically adjustable by a manually operated hydraulic pump. A base platform is horizontally supported by the upper end of the vertically adjustable shaft. A generally vertical tubular column is supported by one end portion of the platform and in turn, intermediate its ends, supports a seat for the patient with patient arm supports secured to the upper end of the column. A pair of obtuse angle torso support bars are telescopically received at one end portion by sockets on opposing sides of the platform. Padded torso supports, extending transversely between the other end portion of the torso support bars form a backrest for the patient when seated upon the seat and form a torso support and head support when these bars are inverted to support the patient in a supine position. Foot rests, adjustably secured to the pedestal base, support the feet and legs when the patient is seated. A pair of telescoping tube supports are removably received by the legs of a U-shaped socket forming member pivotally connected with the platform for vertical pivoting movement of the pair of tubes about a horizontal axis. Feet enveloping members, slidably secured to an arcuate bar removably connected with the telescoping tubes, support the feet of the patient when in a supine position.

The principal object of the invention is to provide a cast chair and spica table occupying a minimum of space in which the device provides a support for a patient, when seated or supine, and disposing and supporting his limbs in any desired position thus permitting casting of upper and lower extremities and casting the torso.

BRIEF DESCRIPTION OF THE DRAWINGS

FIG. 3 is a fragmentary perspective view, to a larger scale, illustrating the manner in which the torso support bars and leg support tubes are connected with the base platform;

DESCRIPTION OF THE PREFERRED EMBODIMENTS

Figure 1:
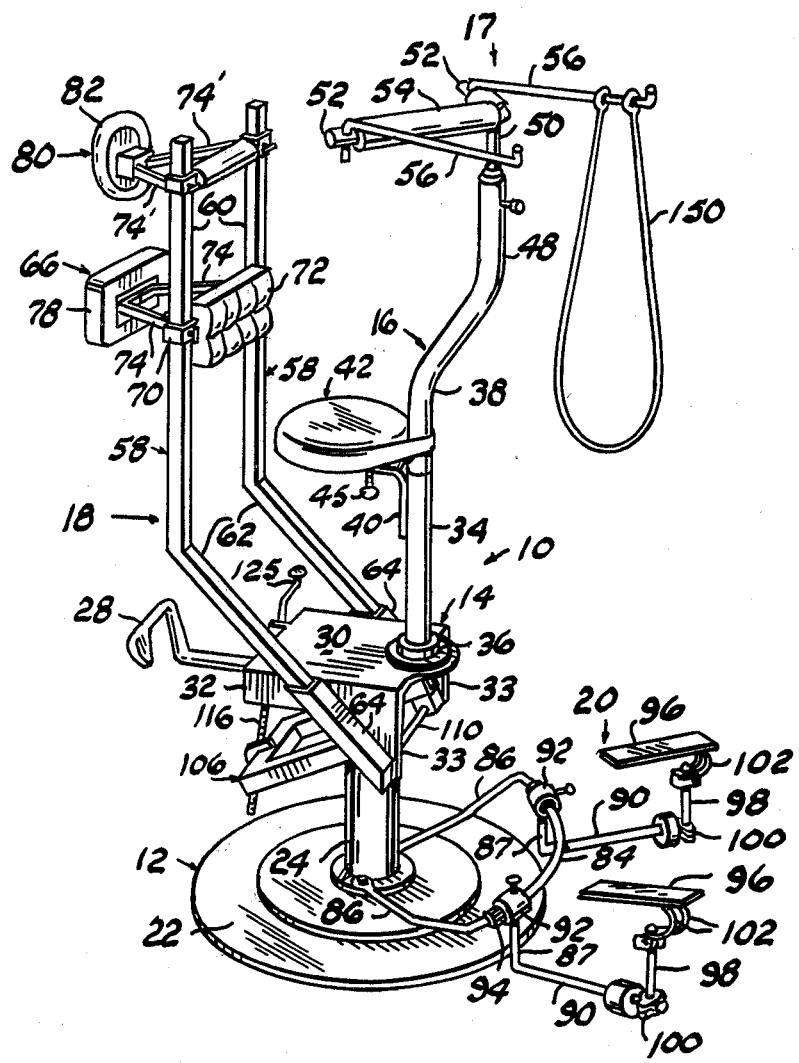
FIG. 1 is a perspective view of the device in cast chair position.
Figure 6:
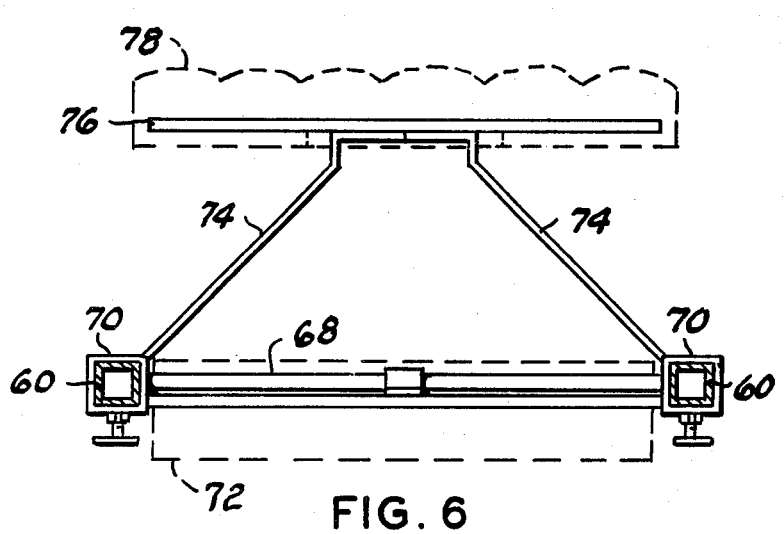
FIG. 6 is an elevational view, partially in section, to another scale, looking in the direction of the arrows 6—6 of FIG. 2; and, FIG. 7 is a fragmentary perspective view, of one of the foot supports.

Like characters of reference designate like parts in those figures of the drawings in which they occur.

In the drawings:

Referring more particularly to FIG. 1, the reference numeral 10 indicates the cast chair embodiment of the device comprising a pedestal base means 12 supporting a platform means 14 in turn supporting a generally vertical column means 16 having arm/leg support means 17 and torso support means 18. The base 12 also supports foot rest means 20. The base means 12 comprises a circular base 22 of a selected radius centrally supporting a dado 24 having a central shaft 26 moved vertically by a lever 28 operating a hydraulic pump means, not shown. In the example shown, the base means 12 is the base portion of a barber chair which normally disposes the upper horizontal surface of a seat 42 (as presently described) approximately 29 inches (73.66 cm) above a floor. The upper end of the vertically movable shaft 26 is secured to a horizontally disposed base platform 30, such as a length of channel iron, having its legs 32 vertically disposed in depending relation and provided at their forward ends with depending panels 33 for the purposes presently explained.

The column means 16 comprises a lower column tube 34 secured to the forward end portion of the platform 30 by a threaded flange 36, or the like, and an upper tube 38 slip joint connected in upstanding relation to the lower column 34. A right angular strap bracket 40 has one of its legs vertically secured, as by welding, to the upper end portion of the lower column tube 34 with the other leg of the strap bracket horizontally overhanging the platform 30.

Figure 5:
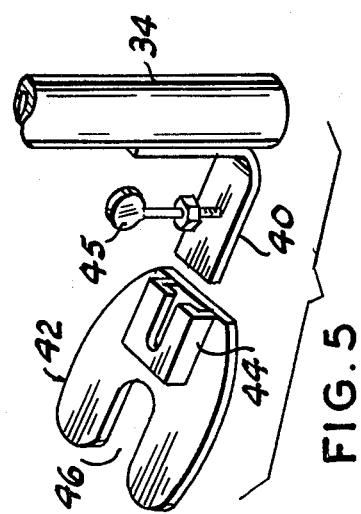
FIG. 5 is an inverted, partially exploded, perspective view of the seat and a portion of the column.
Figure 4:
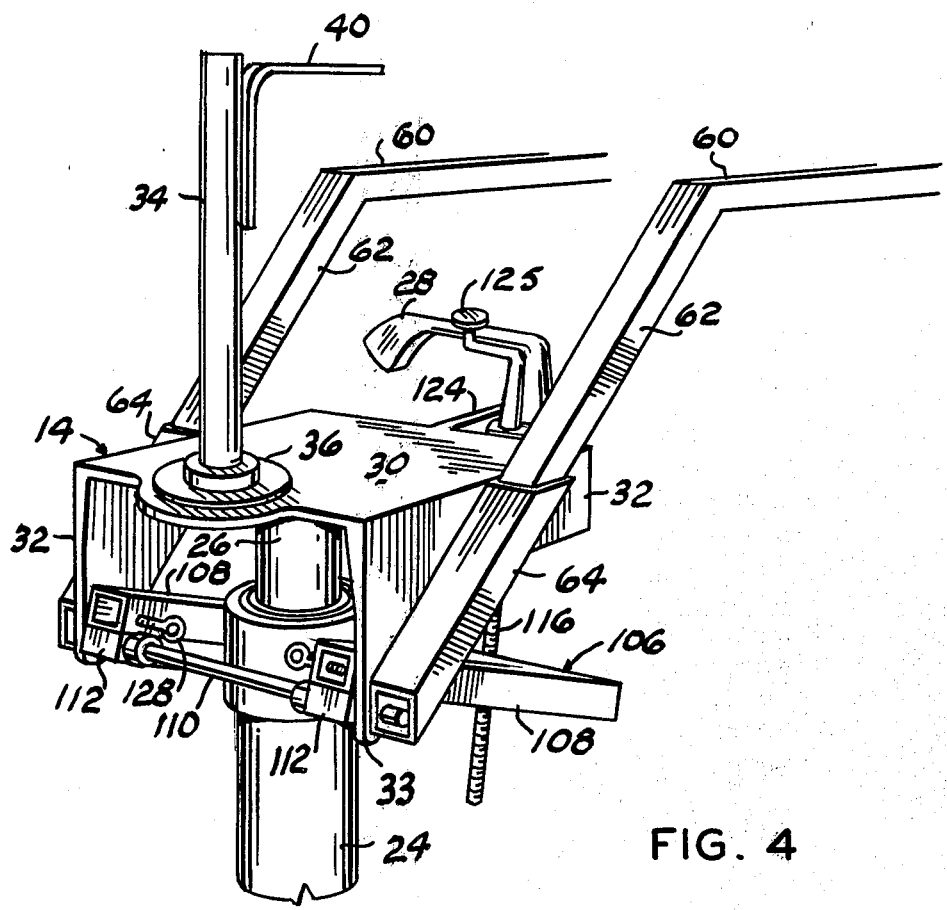
FIG. 4 is a fragmentary perspective view of the components of FIG. 3 when viewed from another direction with the leg supporting tubes removed for clarity.

A generally circular seat 42 (FIG. 2) is provided with a cooperating socket member 44 on its depending flat surface (FIG. 5) for cooperative reception of the horizontal leg of the bracket 40 thus horizontally supporting the seat 42. As seen in FIG. 5, a nut equipped thumb screw 45, entering a slot formed in the member 44, releaseably holds the seat in place, the seat being normally covered by suitable padding, as illustrated by FIG. 1. That end portion of the seat 42 opposite the column tube 34 is centrally slotted, as at 46, for the comfort of the patient when seated or lying on the seat.

The column upper tube 38 is arcuately bent in two vertically spaced-apart positions intermediate its ends so that its upper end portion 48 is offset forwardly of the seat. This upper end portion 38 of the column telescopically receives the arm/leg support means 17 which comprises a short rod 50 secured at its upper end to the apex of a horizontally disposed widened V-shaped bracket 52 opening in a rearward direction and preferably padded, as at 54, for supporting the arms of a patient when seated on the seat 42. A pair of arm/leg support rods 56 are pivotally supported at one end for horizontal movement by the legs of the V-shaped member for supporting the forearms of the patient and/or supporting the legs of the patient, as hereinafter explained.

The torso support means 18 comprises a pair of identical tubular members, which may be bars and are herein referred to as torso bars, preferably square in transverse section, which are formed or bent intermediate their ends to describe equal obtuse angles thus forming torso bar end portions 60 and platform engaging end portions 62. The end portions 60 and 62 of each bar 58 lie in a common plane. The end portions 60 are telescopically received within a pair of sockets 64, formed from similar square tubular material of a cooperating larger size, secured to the outer surfaces of the platform legs 32 and panels 33 on a predetermined angle with respect to the horizontal upper surface of the platform 30, so that the end portions 60 are disposed vertically when the bars 58 are in the cast chair position of FIG. 1.

A torso or back support means 66 is vertically adjustably supported by the bar end portions 60 and comprises a rod 68 connected at its respective ends with a pair of bar clamps 70 which surround and grip the bar end portions 60 at a selected location. A pad 72 is secured to the rod 68 for supporting the patient's back when seated on the seat 42. The support means 66 further includes a pair of braces 74 connected at one end with the clamps 70 and converge at their other ends and are connected with a plate 76 parallel with the rod 68 which supports back padding 78 for supporting the patient's torso when the device is in the spica table position, as presently explained.

A patient head support means 80, similar to the torso support means 66, is similarly slidably received by the bar end portions 60 above the back support means 66, as viewed in FIG. 1. The head support means 80 is characterized by a head pad 82 supported by the converging braces 74'.

Figure 2:
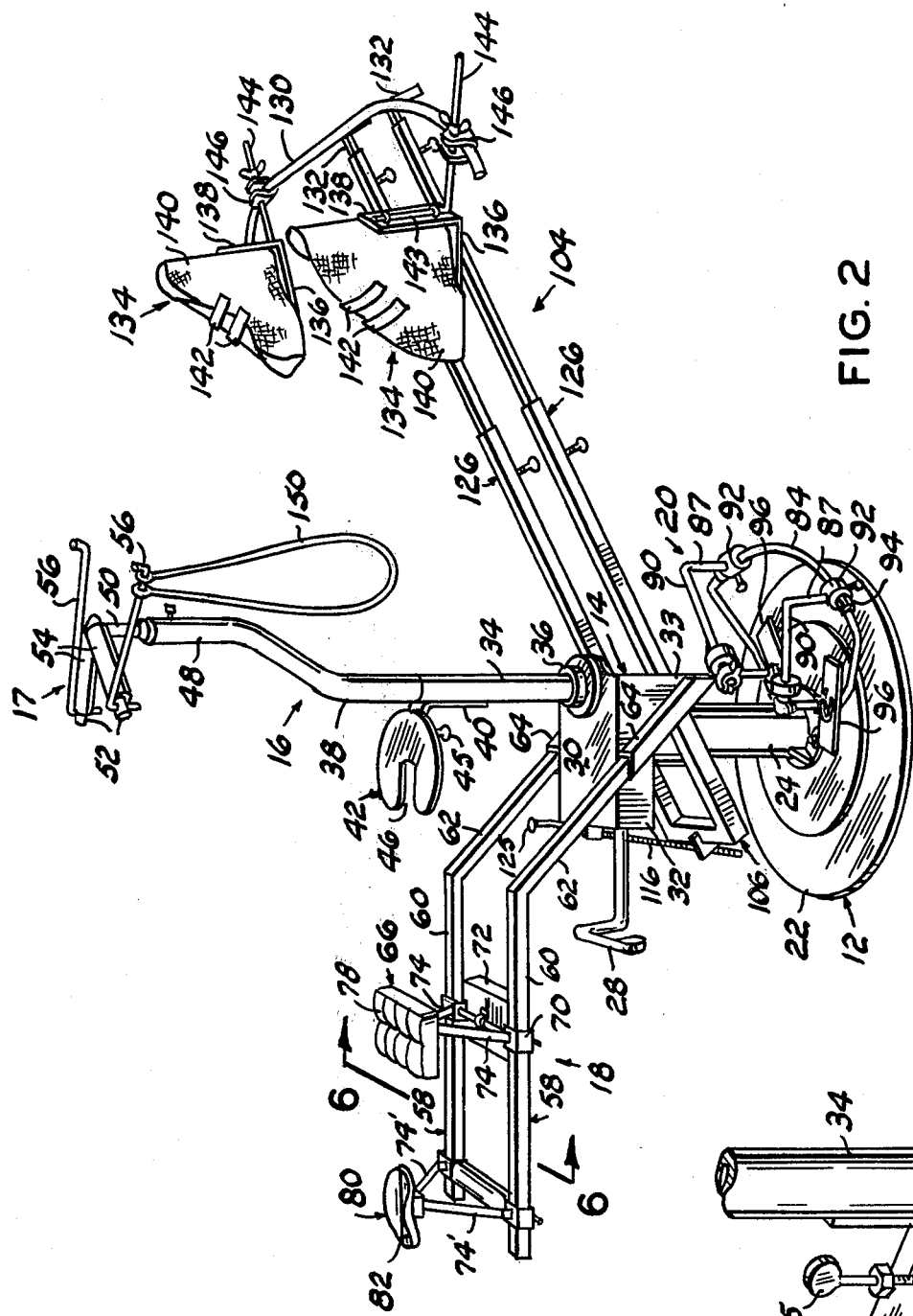
FIG. 2 is a perspective view of the device in spica table position.

The foot support means 20 comprises a part circular rod 84 formed on a radius substantially equal with the base 22 and extending through an arc of less than 180° with its end portions 86 turned inwardly and downwardly in converging relation and secured to the base 22 on opposing sides of the dado 24 for disposing the circular portion of the rod in spaced relation with respect to a common supporting surface forwardly of the vertical axis of the base dado. The foot rest or support means 20 further includes a pair of L-shaped rods, each having one end portion 87 pivotally connected with the circular portion of the rod 84 for vertical pivoting movement of their other end portion 90 about a horizontal axis and held in a selected vertically adjusted position by an internally splined sleeve 92 slidably received by a splined shaft 94 surrounding an intermediate length of the circular portion of the rod 84. A pair of patient foot support panels 96 are secured to the respective leg 90 by a short tube 98 substantially equal in length to the end portions 87 and connected at one end with the respective end portion 90 by a clamp 100 permitting the respective rod to be pivoted in opposing directions about the axis of the end portion 90. The foot panels 96 are similarly connected with the other end portion of the respective rod portion 98 for longitudinal tilting movement toward and away from the common supporting surface by arcuate wire-like rods 102. As shown by FIG. 2, the foot supporting panels 96 and their L-shaped support rods may be pivoted toward and overlie the base in an out-of-the-way position when the device is used as a spica table.

When converting the device to the spica table position of FIG. 2, the torso supporting means 18 is removed, from the platform 30, as a unit with the back and head support means 66 and 80, and inverted with the bar end portions 62 reinserted into the sockets 64 to dispose the bar end portions 60 in a horizontal plane wherein the back support pad 78 and head support 82 lie in the plane of the seat 42. Patient leg and foot extension tube means 104 is then connected with the platform 30. The leg extension means 104 includes a U-shaped member 106, formed from tubular material, square in transverse section in the example shown, having parallel legs 108 pivotally connected with the inner surfaces of the platform panels 33 by a rod 110 extending transversely between the panels 33 and projecting into the depending end portion of each socket 64 so that the respective end portions of the rod 110 form a stop limiting movement of the bar end portions 62 into the sockets 64.

The bight portion 114 of the U-shaped member 106 is centrally connected with a screw threaded rod 116, intermediate its ends, by a threaded lug 118 pivotally connected with a bracket 120 mounted on the bight portion. The upper crank end portion of the rod 116 is journalled by a lug 122 pivotally connected with a bracket 124 centrally secured to the rearward edge of the platform 30. By manually rotating the crank handle 125 about the axis of the rod 116 the U-shaped member 106 is thus pivoted vertically about the horizontal axis of its support rod 110 for the purpose presently explained.

The leg extension means 104 further includes two pairs of telescoping tubes 126, each having one end portion telescopically received cooperatively within the socket forming legs 108 of the U-shaped member 106. Set screws 128 hold the tubes 126 in a selected position in the U-shaped socket legs 108. An elongated rod, having a substantially straight intermediate portion 130, is connected intermediate its ends with a pair of spaced-apart substantially Z-shaped members 132, each having one end portion telescopically received within the cooperating pairs of telescoping tubes 126 at their ends opposite the platform 30 which transversely supports the straight rod portion 130 in parallel spaced relation above the plane of the telescoping pairs of tubes 126. The respective end portions of the rod 130 are extended and arcuately curved in a common plane and on a selected radius toward the vertical axis of the column means 16.

Patient foot enveloping and support means 134 are supported by the respective arcuate end portion of the rod 130 and each comprise a substantially L-shaped strap metal member having a horizontal leg 136 and a substantially vertical leg 138 so that the horizontal leg 136 supports the patient's heel, not shown, with the bottom of his foot substantially parallel and adjacent the upstanding portion 138. A section of fabric 140, secured to the L-shaped member, transversely substantially envelopes the foot of the patient and is secured across his instep by straps 142. The upright member 138 is connected with the foot portion 143 of an L-shaped rod for horizontal pivoting movement about the axis of the rod portion 143. The other end portion 144 of the rod is secured by a clamp 146 to the respective arcuate end portion of the rod 130 for adjustably positioning the clamp longitudinally of the rod and permitting rotation of the rod 144 about its longitudinal axis and vertical pivoting movement of the rod end portion 144 and clamp 146 about the axis of the arcuate portion of the rod 130.

Operation

In operation, when using the device as a cast chair, as shown by FIG. 1, the torso support means 18 is positioned, as shown, and the foot support means 20 disposed substantially as shown. The upper portion 38 of the column means 16 is removed from the depending tube portion 34 thus permitting the patient to seat himself on the seat 42 by moving backwardly from the forward side of the device. The upper portion 38 is then reinserted into the tube 34 and the back support means 66 adjusted for comfort. Either one or both of the foot means 20 are then adjusted about the respective pivoting axes to support the foot and leg or legs of the patient as desired. A flexible cord 150, or the like, connected at its respective ends with either of the arm/leg support rods 56 may be entrained, intermediate its ends, in loop fashion under the leg, not shown, of a patient to support the patient's leg.

When the device is used in the spica table version, illustrated by FIG. 2, the upper portion 38 of the column means 16 is similarly removed. The torso support means 18 is supported by the sockets 64 in the manner illustrated and described hereinabove. The leg extension means 104 is then connected with the U-shaped socket forming member 106 with the tubular extensions 126 vertically adjusted by rotation of the crank rod 116. With the patient lying on the device with his buttocks supported by the seat 42 and torso supported by the pad 78 and head lying on the head rest 82, the patient's feet are placed within the fabric 140 and secured. Similarly, the cord 150 may be employed to support either or both legs of the patient while supine. The foot support means 134 are adjusted with the requirements of the patient's feet or legs, and, if traction is needed on the feet or legs, the tubular members 136 may be telescopically extended or the rods 144 moved longitudinally in their clamps 146.

Obviously the invention is susceptible to changes or alterations without defeating its practicability. Therefore, I do not wish to be confined to the preferred embodiment shown in the drawings and described herein.

I claim:

1. A combination cast chair and spica table, comprising:
   base means including an upright shaft;
   platform means horizontally overlying said shaft;
   generally vertical column means supported by said platform means;
   a seat horizontally supported by said column means intermediate its ends;
   torso support means including a pair of parallel bars connected with said platform means for forming an upright back rest adjacent said seat and opposite said column means when in one position and forming a horizontal torso support lying in the horizontal plane of said seat when in another position; and,
   vertically adjustable and extensible feet and leg support means for supporting the feet and legs of a patient.

2. The combination according to claim 1 in which said platform means comprises:
   a channel-like platform having depending leg-like panels at one of its ends and having an elongated socket forming member on its opposing sides extending angularly upward in parallel relation from the lower limit of said panels toward the other end of said platform.

3. The combination according to claim 2 in which said torso support means comprises:
   a pair of parallel obtuse angle bars each having one platform end portion telescopically received by the respective platform sockets and each having an opposite torso supporting end portion;
   back support means including at least one padding covered back panel extending transversely between said bars intermediate the ends of their torso supporting end portions; and,
   head rest means including at least one head pad extending transversely between said bars adjacent their ends opposite said platform.

4. The combination according to claim 3 in which said column means comprises:
   a lower tube supported by the end portion of said platform having the leg-like panels;
   a seat supporting bracket secured to the upper end portion of said lower tube;
   an upper tube coaxially supported by said lower tube; and,
   arm/leg supporting means secured to the upper end portion of said upper tube,
      said arm/leg supporting means including a horizontally disposed V-shaped member connected by its apex with the upper end of said upper tube, and a pair of horizontally disposed rods respectively pivotally secured, at one end portion for horizontal pivoting movement, with the respective end portion of said V-shaped member.

5. The combination according to claim 4 in which said feet and leg support means comprises:
   a part circular rod extending through an arc of less than 180° secured to said base means in parallel spaced relation with respect to a supporting surface common to said base means;
   a pair of L-shaped rods adjustably secured at one end to said part circular rod for vertical pivoting movement about a horizontal axis; and,
   a pair of foot support panels adjustably secured to the respective other end portions of said L-shaped rods for vertical pivoting movement about a horizontal axis and lateral pivoting movement about the axis of said other end portion of the L-shaped rods.

6. The combination according to claim 4 in which said feet and leg support means comprises:
   a U-shaped member having a bight portion and having tubular legs straddling said upright shaft and pivotally secured for vertical pivoting movement about a horizontal axis at their respective end portions to the inner surface of the depending end portions of said platform leg-like panels;
   two pairs of telescoping tubes each having one end portion telescopically received by the respective U-shaped member tubular leg;
   an elongated rod having arcuate end portions lying in a common plane and curved toward the vertical axis of said column means and extending transversely between and secured to the ends of said two pairs of tubes opposite the U-shaped member;
   a pair of L-shaped rods each having a generally vertically disposed foot portion and each having a leg portion adjustably connected intermediate its ends with an intermediate portion of the respective arcuate rod end portion for vertical pivoting movement about the axis of the arcuate rod end portion and angular rotative movement in opposing directions about the longitudinal axis of its leg end portion;

a pair of L-shaped strap members each having a vertically disposed leg portion pivotally connected with the foot portion of the respective rod of said pair of L-shaped rods for horizontal pivoting movement about the axis of the respective L-shaped rod foot portion; and, fabric means secured to each member of said pair of strap members for enveloping the foot of a patient when disposed therein.

7. The combination according to claim 6 and further including:

crank rod means secured at one end portion to said platform at its end portion opposite said column means for angular rotation about the longitudinal axis of the crank rod, the other end portion of said crank rod being threadedly connected with the bight portion of said U-shaped member for movement of the latter toward and away from said platform.

8. The combination according to claim 5 or 7 in which said base means comprises:

a pedestal base having a dado supporting said vertical shaft; and, hydraulic pump means contained by said base including a manually operated pump and hydraulic fluid release handle for lifting and lowering said vertical shaft.

9. The combination according to claim 5 or 7 and further including:

an elongated flexible element secured in depending loop forming fashion with at least one rod of said horizontally disposed rods.

* * * * *